(12) United States Patent
Siekmann

(10) Patent No.: US 6,287,279 B1
(45) Date of Patent: Sep. 11, 2001

(54) UNIVERSAL SAFETY SYRINGE

(75) Inventor: Manfred Siekmann, Neumunster (DE)

(73) Assignee: Siekmann GmbH, Neumunster (DE)

( * ) Notice: Subject to any disclaimer, the term of this patent is extended or adjusted under 35 U.S.C. 154(b) by 0 days.

(21) Appl. No.: 09/367,249

(22) PCT Filed: Feb. 4, 1998

(86) PCT No.: PCT/DE98/00304

§ 371 Date: Aug. 10, 1999

§ 102(e) Date: Aug. 10, 1999

(87) PCT Pub. No.: WO98/35713

PCT Pub. Date: Aug. 20, 1998

(30) Foreign Application Priority Data

Feb. 15, 1997 (DE) .............................................. 197 05 892

(51) Int. Cl.$^7$ ..................................................... A61M 5/00
(52) U.S. Cl. ........................... 604/110; 604/195; 604/198
(58) Field of Search ................................ 604/27, 36, 38, 604/93, 110, 181, 187, 192, 197, 218, 225, 240–243, 263, 264; 222/630–631

(56) References Cited

U.S. PATENT DOCUMENTS

| | | | |
|---|---|---|---|
| 3,370,588 | * | 2/1968 | Burke . |
| 3,881,484 | * | 5/1975 | Gidcomb et al. . |
| 5,152,750 | * | 10/1992 | Haining ................................ 604/195 |
| 5,328,475 | * | 7/1994 | Chen .................................... 604/110 |
| 5,344,403 | * | 9/1994 | Lee . |
| 5,401,246 | * | 3/1995 | Mazur et al. ........................ 604/110 |
| 5,569,203 | * | 10/1996 | Chen . |
| 5,578,015 | * | 11/1996 | Robb . |

* cited by examiner

*Primary Examiner*—Sharon Kennedy
*Assistant Examiner*—Catherine Serke
(74) *Attorney, Agent, or Firm*—Larson & Larson, P.A.; James E. Larson

(57) ABSTRACT

Universal safety syringe having a protective cap, a cylinder, a plunger and a cannula mounted on a cannula base, it being the case that the cannula base is designed such that it can be pushed firmly against a stop in the protective cap, that the protective cap, which can be pushed externally onto a cone, corresponding to a Luer cone, of the cylinder, is provided with a narrowed section, which is provided on the inside of the cap, in front of a recess designed for receiving the cannula base, and delimits the push on travel, that a recess which receives a cannula base is provided with an undercut which prevents the cannula base from being removed in the forward direction, and with an undercut of which the effect can be overcome by the cone being widened from the inside and which is provided for safeguarding the cannula stop from being pushed in unintentionally during insertion of the syringe, and it also being the case that the plunger is designed with a section which widens the cone cylindrically and with a mushroom-shaped plunger head, which comes into pulling contact with the needle stop. A preferred embodiment provides a safeguard against the plunger being unintentionally pushed in too early and too far.

7 Claims, 4 Drawing Sheets

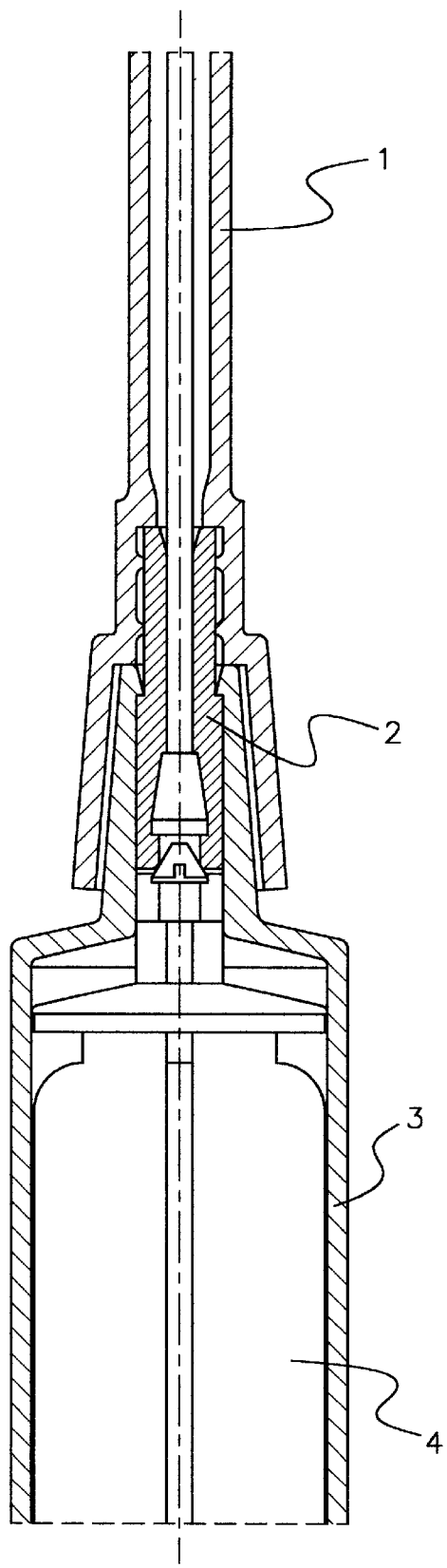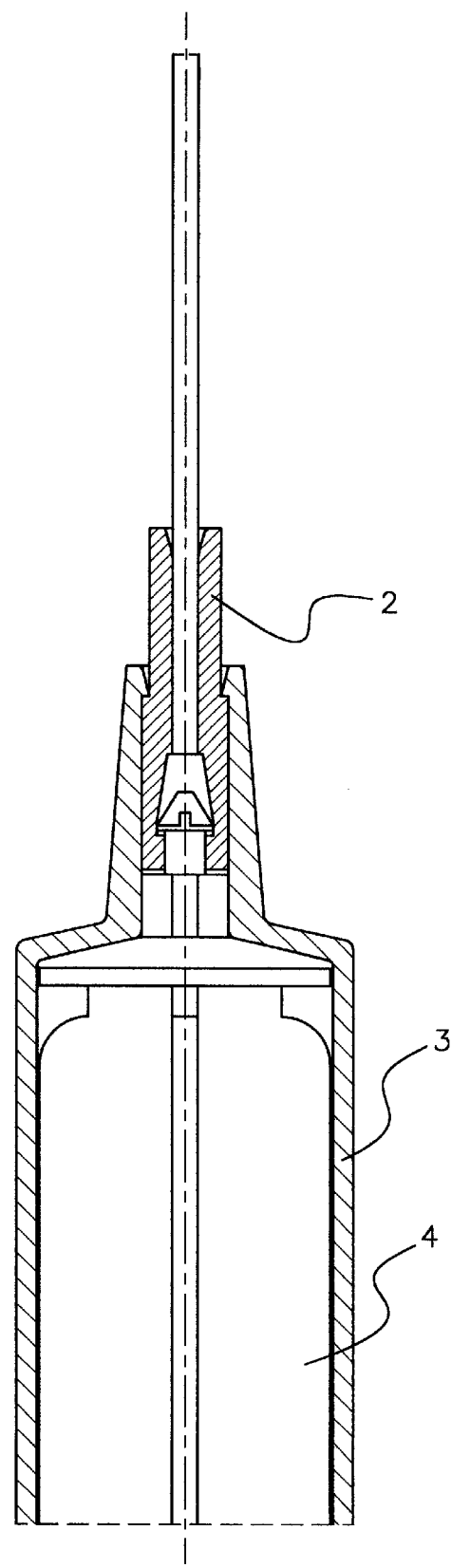
*Fig.1*  *Fig.2*

UNIVERSAL SAFETY SYRINGE

PRIOR APPLICATIONS

This application is a §317 U.S. National Phase application which bases priority on International Application No. PCT/DE98/0034, filed Feb. 4, 1998, which in turn bases priority on German Application No. DE 197 05 892.2, filed Feb. 15, 1997.

BACKGROUND OF INVENTION

1. Field of Invention

The invention relates to a universal safety syringe according to the preamble of the main claim.

2. Description of Prior Art

In the case of a number of safety syringes, as are disclosed, for example, in German Patent Specification 43 40 082, the injection cannulas are moved back into the cylinder, after use, in order to remain there permanently and safely, without there being any risk of injury, during further handling of the syringe. However, as in the abovementioned document, a new material is also usually proposed, in this case an elastomeric material for example, or it is no longer possible to use the conventional needles with Luer cone.

In other embodiments, for example the version described in U.S. Pat. No. 5,336,198, even separate means are proposed for the purpose of tilting the cannula laterally in the cylinder in order that it cannot be pushed out again. Unfortunately, all these proposals have in common a not inconsiderable degree of complexity, which makes these safety syringes appear expensive and suitable only for special applications.

Unfortunately, however, there is such a great demand for safety syringes within the medical profession today that safety syringes really have to be in constant use. Up until now, the complex geometries with which the cannulas and/or syringes have been provided has meant that this has not been possible.

In order, however, for it to be possible for safety syringes with a retractable cannula to be established for general usage, a necessary precondition is so-called "downward" compatibility with material which has been used up until now, so that it is also possible to fit the wide variety of cannulas which have been available up until now. Otherwise, it would be necessary for novel cannulas of all sizes to be provided immediately for all conceivable purposes and at all use locations, in order to avoid the two systems coexisting over a transition period—with myriad possibilities of confusion, and problems with storage of double stocks and differing handling methods at the same time.

However, since hitherto known safety syringes require their own cannulas and cannula bases in each case, although it has frequently not been possible to provide or reproach [sic] the desired variety of these, it is essential for it to be possible to continue using the cannulas which have been used up until now.

If, however, use is made of a universal safety syringe with retractable cannula, careless handling of the plunger may cause the latter to be pushed forwards in the cylinder, where it comes into contact with the cannula base before the syringe is actually used. This can take place, for example, as the cannula is pushed on. It goes without saying, however, that it is absolutely essential for this to be avoided because, even during further filling of the syringe, the cannula base is drawn back (too early) into the cylinder - and it is precisely in emergency situations that this may initially go unnoticed.

In the case of hitherto known safety syringes, for example those in DE 38 44 150, this has been avoided by safety elements which were removed prior to injection, in order for it to be possible for the plunger to be pushed right in. For universal usage, however, separate safety elements are highly undesirable since they not only increase the costs of the syringes, but also render handling of the syringes for hitherto conventional usage more complex.

SUMMARY OF THE INVENTION

According to the invention, then, the disadvantages of the prior art are eliminated by a universal safety syringe having the features of the main claim. Advantageous embodiments of the invention can be gathered from the subclaims.

It is advantageous, in particular, that, in contrast to conventional syringes, the safety syringe does not have any additional part, and it is thus not only the case that the novel safety syringe constitutes the most cost-effective safety syringe solution, but also that the movements involved in handling it are exactly the same as those for handling the conventional syringe. All conventional cannulas can be fitted by way of the outer Luer standard cone provided. Since the principle does not require a prefitted cannula, it is also possible, however, for appropriate (safety) cannulas on their cannula bases to be selected and inserted just prior to use.

The safety syringe described thus corresponds both to DIN 13098 and to ISO 7886. It is advantageous, in particular, that, in a preferred embodiment, a premature pushing-down action, which could render the syringe unusable, is not possible. In the case of an eccentric cone arrangement, a guide groove or, as proposed, two guide grooves located opposite one another can make it possible to use, for this case as well, the principle according to the invention, which, moreover, is suitable not only for all syringe sizes, but also for two-part and three-part syringes with an additional elastic plunger seal at the end of the plunger.

The universal safety syringe according to the invention is distinguished by a cannula base which is pushed firmly against a stop in the protective cap, and also [lacuna] a protective cap which can be pushed externally onto a cone, corresponding to a Luer cone, of the cylinder, there being provided on the inside of the cap, in front of a recess designed for receiving the cannula base, a narrowed section which delimits the push-on travel.

The recess which receives the cannula base [lacuna] provided with an undercut which prevents the cannula base from being removed in the forward direction, and with an undercut of which the effect can be overcome by the cone being widened from the inside and which is provided for safeguarding the cannula base against being pushed in unintentionally during insertion of the syringe, this latter undercut being widened by a cylindrical end of the plunger during the final advancement stage, while a preferably mushroomshaped plunger head is pushed into an essentially cylindrical cavity with border elements engaging behind the mushroom-shaped head.

A further advantageous configuration is distinguished by lugs which are provided at the actuating end of the plunger, are prestressed outwards and, prior to the filling operation, are retained, by corresponding lug supports on the plunger, in a position in which they are aligned essentially along the syringe axis, in order thus to prevent the plunger from being pushed into the cylinder.

Said lugs are designed, for example, as two spreader lugs which are located essentially opposite one another, are fastened at the actuating end of the plunger by film hinges, are oriented towards the cylinder and are initially clamped in a recess, provided at the introduction opening for the plunger, in the cylinder opening for the introduction of the plunger.

Even in the case of an eccentric arrangement of the cone and of the plunger head which grips the cannula holder, the invention can be applied in that the plunger is additionally guided by way of projecting edges in corresponding guide grooves on the inside of the plunger [sic].

DESCRIPTION OF THE DRAWINGS

Further features and advantages of the invention can be gathered from the following description of a preferred exemplary embodiment with reference to the attached drawing, in which:

FIG. 1 shows, in a two-part syringe, the inventive combination of the cannula base in the tip of the cylinder with the protective cap having been pushed on and without the plunger head having been pushed in, FIG. 2 shows an illustration corresponding to FIG. 1 with the plunger head having been pushed in and without the protective cap.

DETAILED DESCRIPTION OF THE PREFERRED EMBODIMENT

Figure 3:
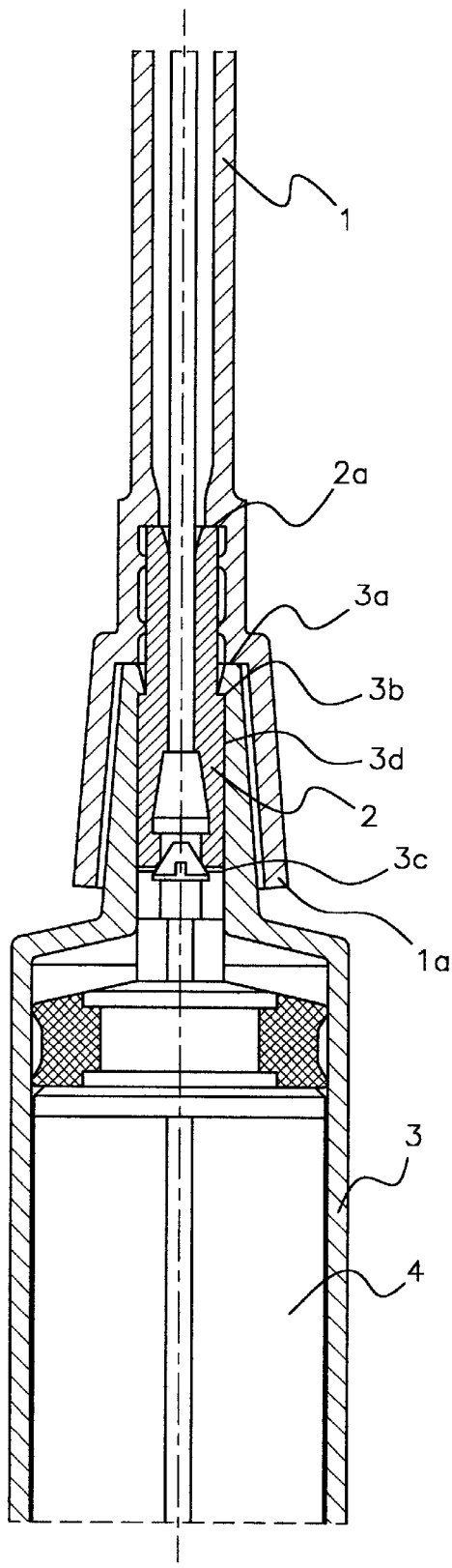
FIG. 3 shows a three-part syringe in an illustration corresponding to FIG. 1.

The syringe illustrated in FIG. 1 is provided with a protective cap 1, which is clamped on a cannula base 2 and, by way of a collar 1a (FIG. 3), fits on a cone on the cylinder which corresponds to the Luer standard. This collar 1a serves, at the same time, as a guide for the introduction of the cannula base 2 when the latter is introduced into the cylinder 3. It protects the cannula base against damage and contamination prior to the introduction.

The cannula base 2 is provided with a stop 2a, which strikes against a corresponding stop of the protective cap 1 when the cannula for the universal safety syringe is fitted. As a result, the protective cap 1 additionally serves as a stop when the cannula base is introduced into the cylinder, in that the position of the cannula base 2 in the cylinder 3 is determined by the protective cap striking against the cylinder at a further stop 3a.

The cylinder 3 is advantageously provided with an undercut 3b which, at the preselected push-in depth, engages behind a corresponding reduction in diameter of the cannula base 2 and thus safeguards against the cannula being drawn out in a forward direction once it has been pushed in. On the other hand, however, a further undercut 3c is also provided as a base in the opposite direction and prevents the base from being pushed in further when the cannula is inserted. However, this base is not as wide as the abovementioned base, but rather is dimensioned precisely such that when an end piece of the plunger, which widens the cylinder slightly at this location, is pushed in, it makes it possible for the cannula base 2 to be drawn inwards, through the widened opening, into the plunger.

There may be additionally provided between the cannula base and cylinder one or more sealing lips 3d, which seal the base at this location.

Figure 4:
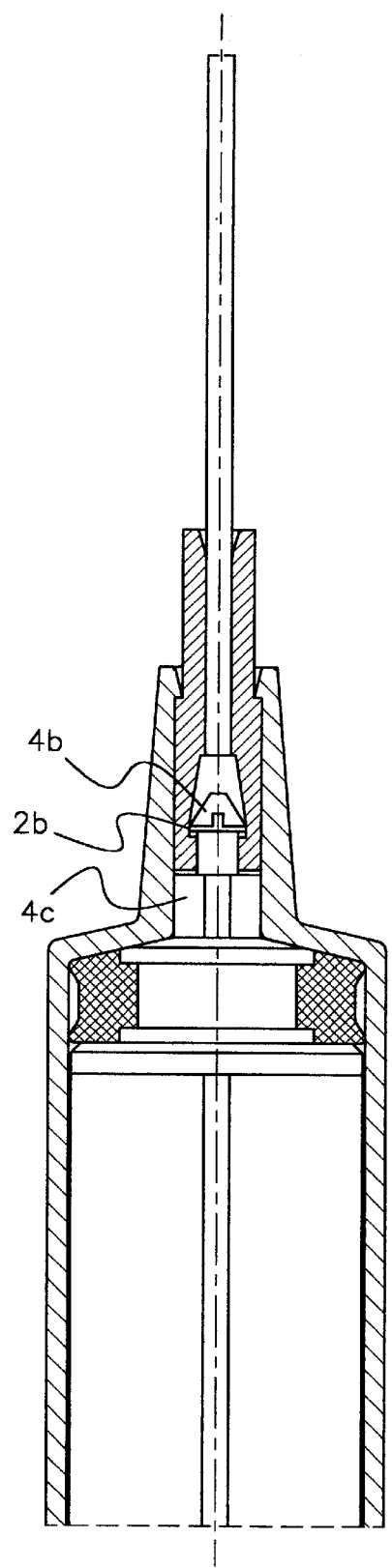
FIG. 4 shows a three-part syringe in an illustration corresponding to FIG. 2.

In FIG. 4, 4c designates the cylindrical part of the plunger which expands the cylinder beneath the seat of the cannula base in order to make it possible to overcome the effect of the undercut 3c when, once a medicament has been discharged, the syringe is to be rendered unusable by the cannula being drawn in. A small amount of play is left between the undercut 2b provided in the cannula base and the plunger head which is introduced here, but this play is sufficient to allow the cannula, in the drawn-back state, to drop to the side under the action of gravity, and thus to be prevented from being able to be pushed out through the same opening again.

Figures 5, 6, 7:
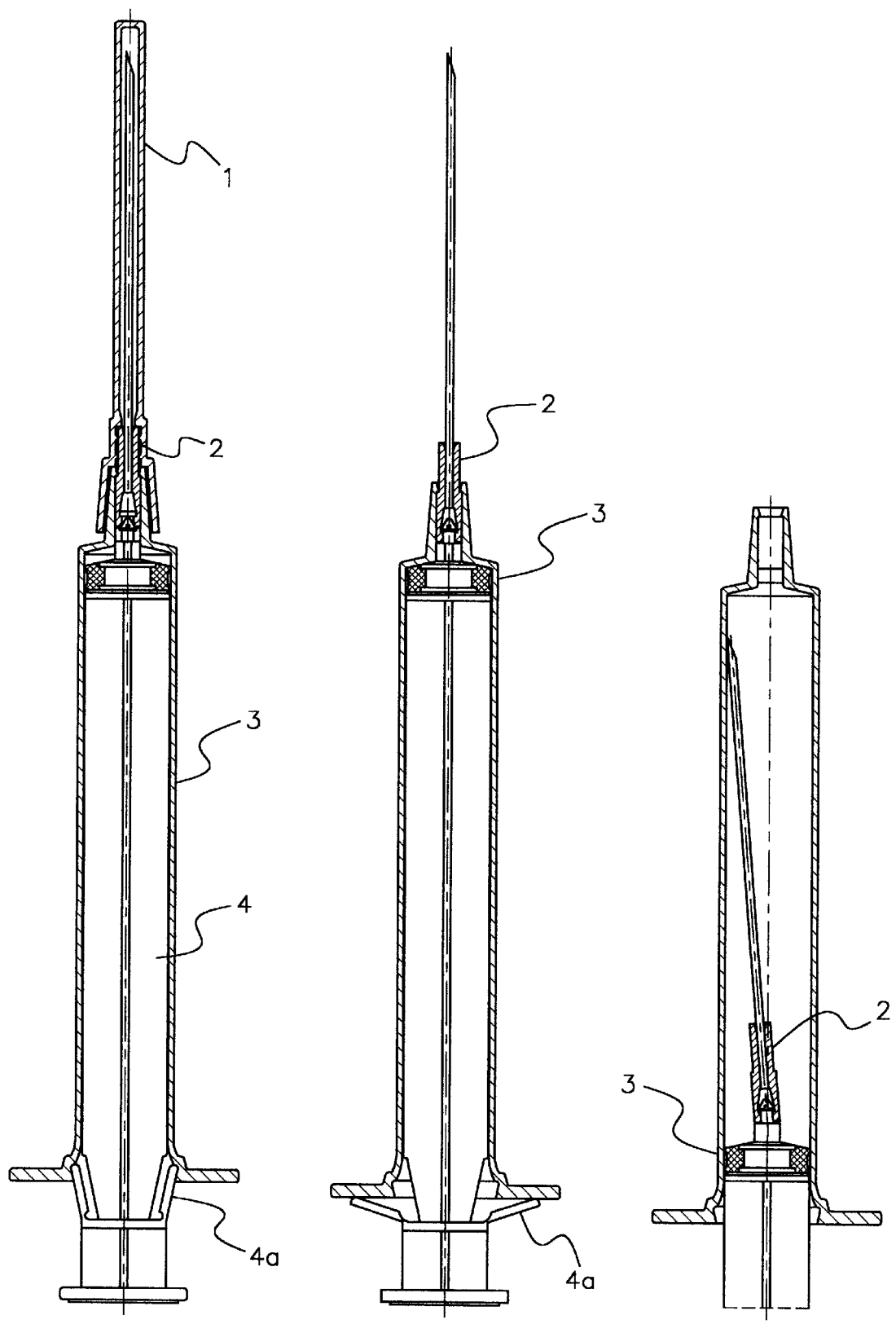
FIG. 5 shows a further preferred exemplary embodiment of the syringe according to the invention with the clamping lugs still mounted in the cylinder.
FIG. 6 shows the illustration of FIG. 5 with the plunger having been pushed in and the clamping lugs having been displaced outwards.
FIG. 7 shows the closed position with the plunger having been drawn out again.

Additionally proposed in a preferred embodiment of the invention illustrated in FIGS. 5 and 6 are two lugs 4a which are provided at the actuating end of the plunger by a film hinge and are latched in a corresponding, for example annular, recess at the open grip-plate end of the cylinder. Provided that the plunger 4 is not moved out, the lugs will remain in a state in which they are stressed outwards, by virtue of their film-hinge prestressing, in the annular recess. If, however, the plunger is drawn back, they will be reliably displaced further outwards, with the result that, when the plunger is pushed in again, they rest flatly on the grip plate, on the outside of the cylinder, rather than returning into the recess again. As a result, the plunger can be pushed in right to the base of the cylinder in order to penetrate into the cannula base by way of the plunger head and to carry said base along with it during a subsequent rearward movement. Prior to a first rearward movement of the plunger, however, forces of virtually any strength can be exerted on the plunger without the latter moving into the stem of the cannula.

Figure 8:
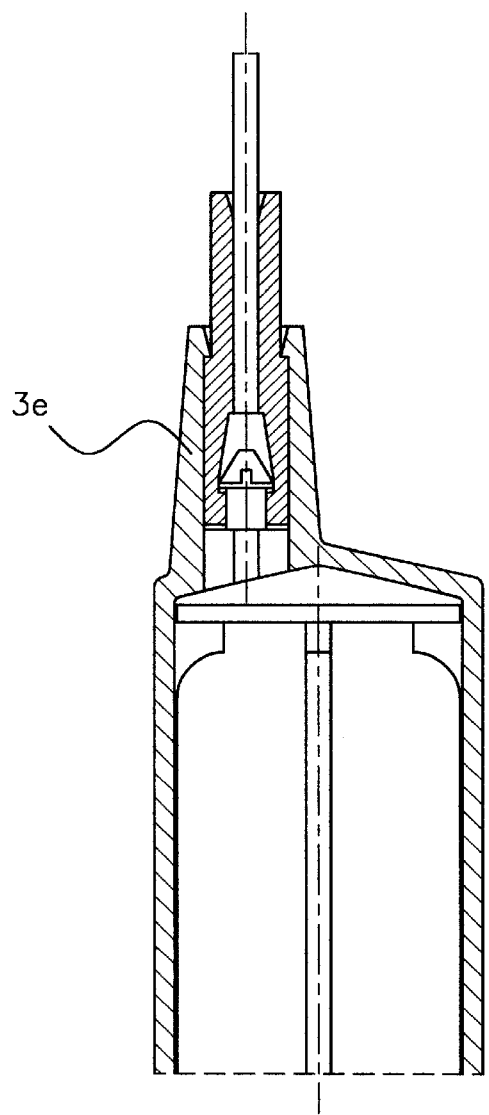
FIG. 8 shows an illustration of an eccentric cone arrangement.
Figure 9:
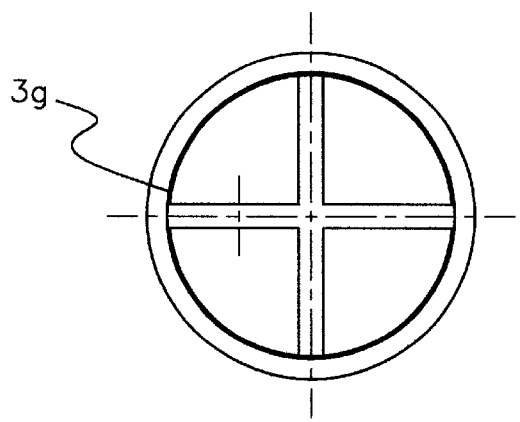
FIG. 9 shows a cross section through the plunger, in which it is possible to see the guide grooves.

Finally, FIG. 8 illustrates an eccentric cone 3e which, nevertheless, can easily be provided with a cannula base in the same way if the plunger is designed in a rotationally fixed manner, for example, by two projecting edges which are guided in corresponding guide grooves 3g [sic] on the inside of the plunger [sic].

In conclusion, all that remains to point out is that the only difference between the embodiments of FIGS. 1 and 2 and those of FIGS. 3 and 4 is an additional elastic sealing ring, which is positioned at the end of the plunger, on the outside, around a corresponding sealing-ring support.

Having thus described the invention, what is claimed and desired to be secured by Letters Patent is:

1. A universal safety syringe having a cylinder, a center axis of the cylinder, a projecting member attached to an end of the cylinder and defining a recess, a plunger inserted within the cylinder and moveable along the center axis, a cannula base inserted within the recess, a cannula mounted on the cannula base and a protective cap for covering the cannula, the cannula base and the projecting member, the improvement comprising:

(a) a first undercut formed proximal to a top portion of the projecting member recess prohibiting the cannula base from being unintentionally removed during removal of the syringe from an insertion destination, (b) a second undercut formed proximal to a bottom portion of the projecting member recess prohibiting the cannula base from being unintentionally pushed into the cylinder during insertion of the syringe into the insertion destination, (c) a mushroom-shaped plunger head capable of entering cavity formed in the cannula base, the plunger having a lower portion for resting against a third undercut once the plunger head has entered the cavity, (d) the projecting member having a conical shape, (e) the protective cap having a first, second and third section, the first section having a greater diameter about a mid-section than the second section and having a conical shape, the second section having a greater diameter than the third section, the first section covering the conical-shaped projecting member, the second section covering the cannula base and the third section covering the cannula, (f) a first stop member of the cannula base, (g) a second stop member of the protective cap, the first and second stop members juxtaposed when the protective cap is completely inserted over the cannula, (h) an expansion section attached below the mushroom-shaped plunger head for widening a lower portion of the projecting member and permitting the cannula base to fall inwardly within the cylinder by the force of gravity, (i) a plurality of lugs located proximal to an actuating end of the plunger, the plurality of lugs capable of expanding outwardly when the plunger is pulled in a direction away from the cannula, but preventing any inward movement of the plunger prior to pulling the plunger away from the cannula, and (j) a plurality of lug supports for retaining the plurality of lugs in a fixed position essentially along the cylinder center axis prior to the syringe being filled with a liquid.

2. The universal safety syringe of claim 1, wherein the cavity formed in the cannula base is essentially cylindrically-shaped.

3. The universal safety syringe of claim 1, wherein the projecting member, the cannula base and the cannula are axially aligned with the center axis of the cylinder.

4. The universal safety syringe of claim 1, wherein the projecting member, the cannula base and the cannula are off-axis from the center axis of the cylinder.

5. The universal safety syringe of claim 4, further comprising:

(a) a plurality of projecting edges of the plunger and (b) a plurality of guide groves formed in the cylinder for receiving the plurality of projecting edges and guiding the plunger through the cylinder.

6. The universal safety syringe of claim 5, wherein the plurality of projecting edges include a pair of projecting edges disposed 180 degrees from one another and the plurality of guide grooves includes a pair of guide grooves disposed 180 degrees from one another.

7. The universal safety syringe of claim 1, wherein a pair of lugs and a pair of lug supports are employed, the pair of lugs and lug supports positioned at 180 degrees from another.

\* \* \* \* \*